United States Patent [19]

Häbich et al.

[11] Patent Number: 5,364,931

[45] Date of Patent: Nov. 15, 1994

[54] PHOSPHONATE-CONTAINING PSEUDOPEPTIDES OF THE HYDROXYETHYLAMINE AND NORSTATIN TYPE

[75] Inventors: Dieter Häbich; Jutta Hansen, both of Wuppertal; Arnold Paessens, Haan, all of Germany

[73] Assignee: Bayer Aktiengesellschaft, Leverkusen, Germany

[21] Appl. No.: 746,271

[22] Filed: Aug. 15, 1991

[30] Foreign Application Priority Data

Aug. 24, 1990 [DE] Germany ............... 4026703
Nov. 1, 1990 [DE] Germany ............... 4034707

[51] Int. Cl.$^5$ ............... C07F 9/58; C07F 9/60; C07F 9/572
[52] U.S. Cl. ............... 530/331; 546/22; 546/23; 548/111
[58] Field of Search ............... 548/111; 530/331; 546/22, 23

[56] References Cited

U.S. PATENT DOCUMENTS 4,186,268  1/1980  Petrillo, Jr. ............... 546/21
4,599,198  7/1986  Hoover ............... 548/334.1

OTHER PUBLICATIONS

J. Med. Chem. 31, 1839 (1988).
J. R. Luily et al., J. Org. Chem. 52, 1487 (1987).
Journal Medicinal Chemistry, vol. 31, No. 3, 1988, pp. 532–539.

Primary Examiner—Alan L. Rotman
Attorney, Agent, or Firm—Sprung Horn Kramer & Woods

[57] ABSTRACT

The invention relates to phosphonate-containing pseudopeptides of the hydroxyethylamine and norstatin type, to new oxirane- and thiirane-containing pseudopeptides as intermediates, to processes for their preparation and to their use as retroviral agents.

6 Claims, No Drawings

PHOSPHONATE-CONTAINING PSEUDOPEPTIDES OF THE HYDROXYETHYLAMINE AND NORSTATIN TYPE

The invention relates to phosphonate-containing pseudopeptides of the hydroxyethylamine and norstatin type, to new oxirane- and thiirane-containing pseudopeptides as intermediates, to processes for their preparation and to their use as retroviral agents.

It has already been attempted to employ pseudopeptides, which in some cases also have renin-inhibitory activity, in combating AIDS [cf. GB A2 203,740; EP 337,714; EP 342,541; EP 346,847 and EP 352,000; EP 354,522; EP 356,223; EP 357,332].

It is additionally known that simple epoxides such as EPNP [1,2-epoxy-3-(4-nitrophenoxy)propane] cause a weak inactivation of HIV-I protease ($IC_{50}$=450 μM) [cf. T. D. Meek et al., in V. Kostha (Editors) "Protease of Retroviruses" Proceedings of the Colloquium C52 14th International Congress of Biochemistry, Prague, Czechoslovakia Jul. 10–15 (1988), Walter de Gruyter 1989]. A reference to peptides is not made therein.

The present invention relates to new phosphonate-containing pseudopeptides of the hydroxyethylamine and norstatin type of the general formula (I)

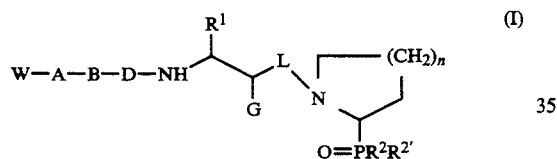

in which

W
  represents hydrogen or a typical amino protecting group, or
  represents straight-chain or branched alkyl or alkenyl in each case having up to 6 carbon atoms, which are optionally substituted by aryl having 6 to 10 carbon atoms, or
  represents a group of the formula $R^3$—CO—, $R^5R^4N$—CO— or $R^6$—$SO_2$—, in which
    $R^3$
      denotes hydrogen, trifluoromethyl or straight-chain or branched alkoxy having up to 8 carbon atoms or alkyl having up to 18 carbon atoms, each of which is optionally monosubstituted or disubstituted by aryl having 6 to 10 carbon atoms or pyridyl, or
      denotes aryl having 6 to 10 carbon atoms, which is optionally substituted by halogen, trifluoromethyl, trifluoromethoxy or by straight-chain or branched alkyl having up to 8 carbon atoms,
      denotes cycloalkyl having 3 to 7 carbon atoms, or
      denotes quinolyl, quinolyl-N-oxide, indolyl, pyridyl, pyridyl-N-oxide, morpholino or piperazinyl, or
      denotes a radical of the formula

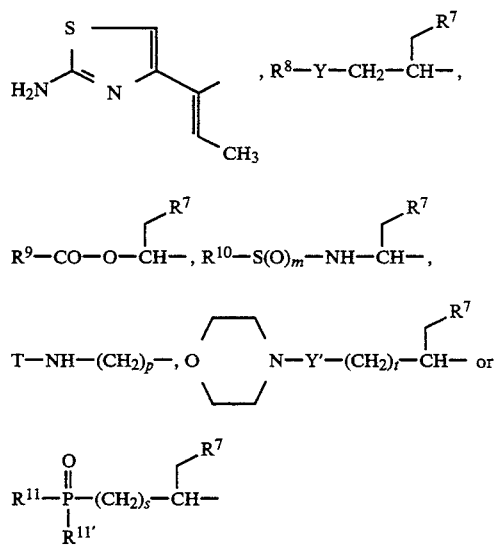

in which
  $R^7$ denotes phenyl or naphthyl,
  $R^8$, $R^9$ and $R^{10}$ are identical or different and denote straight-chain or branched alkyl having up to 14 carbon atoms, which is optionally substituted by phenyl or naphthyl, or denote aryl having 6 to 10 carbon atoms, which is in turn substituted by alkyl having up to 4 carbon atoms,
  m denotes a number 0, 1 or 2,
  T denotes cyclohexyl,
  p denotes a number 1, 2 or 3,
  Y and Y' are identical or different and denote the CO or $SO_2$ group,
  t denotes a number 0 or 1,
  $R^{11}$ and $R^{11'}$ are identical or different and denote hydroxyl or alkoxy having up to 8 carbon atoms,
  s denotes a number 1 or 2,
$R^4$ and $R^5$ are identical or different and
  denote hydrogen or
  denote aryl having 6 to 10 carbon atoms, which is optionally substituted by straight-chain or branched alkyl having up to 6 carbon atoms or halogen, or
  denote cycloalkyl having 3 to 7 carbon atoms, or
  denote straight-chain or branched alkyl having up to 18 carbon atoms,
$R^6$ denotes straight-chain or branched alkyl having up to 8 carbon atoms,
A, B and D are identical or different and
  represent a direct bond or
  represent a radical of the formula

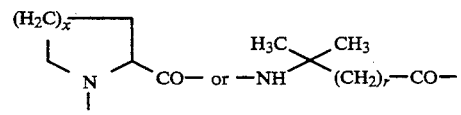

in which
  x denotes the number 1 or 2 and
  r denotes the number 0 or 1, or
represent a group of the formula

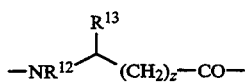

in which
z denotes the number 0 or 1,
R$^{12}$ denotes hydrogen or straight-chain or branched alkyl having up to 4 carbon atoms,
R$^{13}$
 denotes cycloalkyl having 3 to 8 carbon atoms or aryl having 6 to 10 carbon atoms or hydrogen, or
 denotes straight-chain or branched alkyl having up to 8 carbon atoms, which is optionally substituted by methylthio, hydroxyl, mercapto, guanidyl or by a group of the formula —NR$^{14}$R$^{15}$ or R$^{16}$—OC—, in which
  R$^{14}$ and R$^{15}$ are identical or different and denote hydrogen, straight-chain or branched alkyl having up to 8 carbon atoms or phenyl, and
  R$^{16}$ denotes hydroxyl, benzyloxy, alkoxy having up to 6 carbon atoms or the abovementioned group —NR$^{14}$R$^{15}$,
 or which is optionally substituted by cycloalkyl having 3 to 8 carbon atoms or by aryl having 6 to 10 carbon atoms, which in turn is substituted by hydroxyl, halogen, nitro, alkoxy having up to 8 carbon atoms or by the group —NR$^{14}$R$^{15}$, in which
  R$^{14}$ and R$^{15}$ have the abovementioned meaning, or which is optionally substituted by a 5- or 6-membered nitrogen-containing heterocycle or indolyl, in which the corresponding —NH functions are optionally protected by alkyl having up to 6 carbon atoms or by an amino protecting group,
R$^{1}$ represents straight-chain or branched alkyl or alkenyl having up to 10 carbon atoms, which are optionally substituted by cycloalkyl having 3 to 8 carbon atoms or by aryl having 6 to 10 carbon atoms, which can in turn be substituted by halogen, nitro, hydroxyl, amino or straight-chain or branched alkoxy having up to 4 carbon atoms,
n represents the number 1or 2,
R$^{2}$ and R$^{2'}$ are identical or different and
 represent hydroxyl, or
 represent straight-chain or branched alkoxy having up to 4 carbon atoms,
G represents a group of the formula —SH or —OH, and
L represents the —CH$_2$ or —CO group and their physiologically acceptable salts.

The compounds of the general formula (I) according to the invention have several asymmetric carbon atoms. They can be present independently of one another in the D- or the L- form. The invention includes the optical antipodes as well as the isomer mixtures or racemates. Preferably, the groups A, B and D are present independently of one another in the optically pure form, preferably in the L-form.

The radical of the general formula (XII)

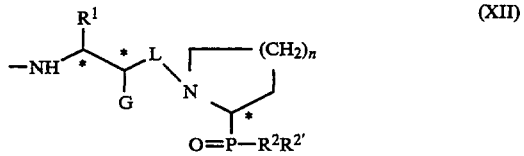

has 3 asymmetric carbon atoms (*), which can be present independently of one another in the R- or S-configuration.

Amino protecting groups in the context of the invention are the amino protecting groups customary in peptide chemistry.

These preferably include: benzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 4-nitrobenzyloxycarbonyl, 2-nitrobenzyloxycarbonyl, 2-nitro-4,5-dimethoxybenzyloxycarbonyl, methoxycarbonyl, ethoxycarbonyl, propoxycarbonyl, isopropoxycarbonyl, butoxycarbonyl, isobutoxycarbonyl, tert-butoxycarbonyl, allyloxycarbonyl, vinyloxycarbonyl, 2-nitrobenzyloxycarbonyl, 3,4,5-trimethoxybenzyloxycarbonyl, methoxycarbonyl, ethoxycarbonyl, propoxycarbonyl, isopropoxycarbonyl, butoxycarbonyl, isobutoxycarbonyl, tert-butoxycarbonyl, cyclohexoxycarbonyl, 1,1-dimethylethoxycarbonyl, adamantylcarbonyl, phthaloyl, 2,2,2-trichloroethoxycarbonyl, 2,2,2-trichloro-tert-butoxycarbonyl, menthyloxycarbonyl, phenoxycarbonyl, 4-nitrophenoxycarbonyl, fluorenyl-9-methoxycarbonyl, formyl, acetyl, propionyl, pivaloyl, 2-chloroacetyl, 2-bromoacetyl, 2,2,2-trifluoroacetyl, 2,2,2-trichloroacetyl, benzoyl, 4-chlorobenzoyl, 4-bromobenzoyl, 4-nitrobenzoyl, phthalimido, isovaleroyl or benzyloxymethylene.

The compounds of the general formula (I) according to the invention can be present in the form of their salts. These can be salts with inorganic or organic acids or bases.

Preferred compounds of the general formula (I) are those in which
W
 represents hydrogen, tert-butyloxycarbonyl (BOC), 9-fluorenylmethyloxycarbonyl (Fmoc) or benzyloxycarbonyl (Z), or
 represents straight-chain or branched alkyl or alkenyl in each case having up to 4 carbon atoms, which are optionally substituted by phenyl, or
 represents a group of the formula R$^{3}$—CO— or R$^{5}$R$^{4}$N—CO— or R$^{6}$—SO$_2$ in which
  R$^{3}$
   denotes hydrogen, trifluoromethyl or straight-chain or branched alkoxy having up to 4 carbon atoms or alkyl having up to 16 carbon atoms, each of which is optionally monosubstituted or disubstituted by phenyl, naphthyl or pyridyl, or
   denotes phenyl or naphthyl, which are optionally substituted by fluorine, chlorine, trifluoromethyl, trifluoromethoxyor by straight-chain or branched alkyl having up to 6 carbon atoms,
   denotes cyclopropyl, cyclopentyl, cyclohexyl, quinolyl—N-oxide, quinolyl, indolyl, pyridyl, pyridyl—N-oxide, morpholino or piperazinyl, or
   denotes a radical of the formula

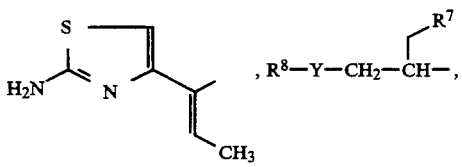

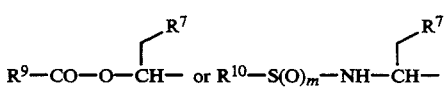

in which
Y denotes the CO or $SO_2$ group,
$R^7$ denotes phenyl or naphthyl,
$R^8$, $R^9$ and $R^{10}$ are identical or different and denote straight-chain or branched alkyl having up to 8 carbon atoms, tolyl, phenyl or naphthyl,
m denotes a number 1 or 2,
$R^4$ and $R^5$ are identical or different and
denote hydrogen or
denote phenyl or naphthyl, which are optionally substituted by straight-chain or branched alkyl having up to 4 carbon atoms, fluorine or chlorine,
denote cyclopropyl, cyclopentyl or cyclohexyl, or
denote straight-chain or branched alkyl having up to 16 carbon atoms,
$R^6$ denotes straight-chain or branched alkyl having up to 6 carbon atoms,
A, B and D are identical or different and
represent a direct bond or
represent proline, or
represent a radical of the formula

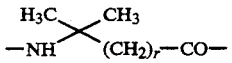

in which r denotes the number 0 or 1,
represent a group of the formula

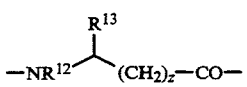

in which
z denotes the number 0 or 1,
$R^{12}$ denotes hydrogen, methyl or ethyl,
$R^{13}$ denotes cyclopentyl, cyclohexyl, phenyl or hydrogen,
or denotes straight-chain or branched alkyl having up to 6 carbon atoms, which can optionally be substituted by methylthio, hydroxyl, mercapto, guanidyl, amino, carboxyl or $H_2N—CO—$, or is substituted by cyclohexyl, naphthyl or phenyl, each of which can in turn be substituted by fluorine, chlorine, hydroxyl, nitro or alkoxy having up to 4 carbon atoms,
or is substituted by indolyl, imidazolyl, pyridyl, triazolyl or pyrazolyl, where the corresponding —NH functions are optionally protected by alkyl having up to 4 carbon atoms or by an amino protecting group,
$R^1$ represents straight-chain or branched alkyl or alkenyl having up to 8 carbon atoms, which are optionally substituted by cyclopropyl, cyclobutyl, cyclopentyl, cyclohexyl, cycloheptyl or phenyl, each of which can in turn be substituted by fluorine, chlorine, bromine, nitro, hydroxyl or amino,
n represents the number 1 or 2,
$R^2$ and $R^{2'}$ are identical or different and
represent hydroxyl, or
represent straight-chain or branched alkoxy having up to 4 carbon atoms,
G represents a group of the formula —SH or —OH and
L represents the —$CH_2$ or —CO group
and their physiologically acceptable salts.

Particularly preferred compounds of the general formula (I) are those in which
W
represents hydrogen, tert-butyloxycarbonyl (BOC) or benzyloxycarbonyl (Z), or
represents allyl or benzyl,
represents a group of the formula $R^3—CO—$, $R^5R^4N—CO—$ or $R^6—SO_2$, in which
$R^3$
denotes hydrogen, trifluoromethyl or straight-chain or branched alkyl having up to 14 carbon atoms, each of which is optionally monosubstituted or disubstituted by phenyl, naphthyl or pyridyl, or
denotes phenyl or naphthyl, which are optionally substituted by fluorine, chlorine, trifluoromethyl, trifluoromethoxy or by straight-chain or branched alkyl having up to 4 carbon atoms,
denotes cyclopropyl, cyclopentyl, cyclohexyl, quinolyl-N-oxide, quinolyl, indolyl, pyridyl, pyridyl-N-oxide, morpholino or piperazinyl, or
denotes a radical of the formula

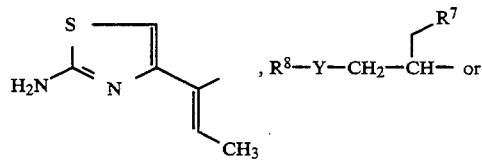

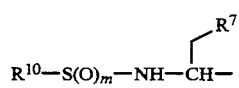

in which
Y denotes the CO or $SO_2$ group,
$R^7$ denotes phenyl or naphthyl,
$R^8$ and $R^{10}$ are identical or different and denote straight-chain or branched alkyl having up to 4 carbon atoms, tolyl, phenyl or naphthyl,
m denotes a number 1 or 2,
$R^4$ and $R^5$ are identical or different and
denote hydrogen or
denote phenyl or naphthyl, each of which is optionally substituted by methyl, fluorine or chlorine,
denote cyclopropyl, cyclopentyl or cyclohexyl, or
denote straight-chain or branched alkyl having up to 14 carbon atoms,
$R^6$ denotes straight-chain or branched alkyl having up to 4 carbon atoms,
A, B and D are identical or different and represent a direct bond, or
represent proline, or
represent a radical of the formula

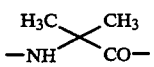

represent a group of the formula

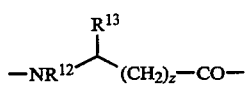

in which
z denotes the number 0 or 1,
$R^{12}$ denotes hydrogen or methyl,
$R^{13}$ denotes cyclopentyl, cyclohexyl or hydrogen,
or denotes straight-chain or branched alkyl having up to 4 carbon atoms, which is optionally substituted by methylthio, hydroxyl, mercapto, guanidyl, amino, carboxyl or $H_2N-CO-$, or is substituted by cyclohexyl, naphthyl or phenyl, each of which can in turn be substituted by fluorine, chlorine or alkoxy having up to 4 carbon atoms, or is substituted by indolyl, imidazolyl, triazolyl, pyridyl or pyrazolyl, where the NH function is optionally protected by methyl, benzyloxymethylene or t-butyloxycarbonyl (Boc),
$R^1$ represents straight-chain or branched alkyl having up to 6 carbon atoms, which is optionally substituted by cyclopropyl, cyclopentyl, cyclohexyl or phenyl, each of which can in turn be substituted by hydroxyl,
n represents the number 1 or 2,
$R^2$ and $R^{2'}$ are identical or different and represent hydroxyl or straight-chain or branched alkoxy having up to 4 carbon atoms,
G represents a group of the formula —SH or —OH and
L represents the —$CH_2$ or —CO group
and their physiologically acceptable salts.

A process for the preparation of the compounds according to the invention of the general formula (I)

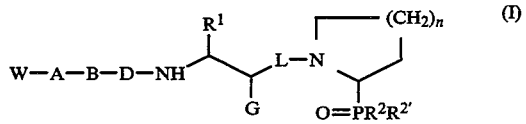

in which W, A, B, D, $R^1$, $R^2$, $R^{2'}$, G, L and n have the abovementioned meaning,
has additionally been found, characterised in that
[A] compounds of the general formula (Ia) or (Ib)

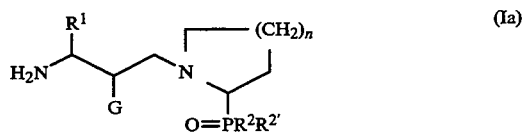

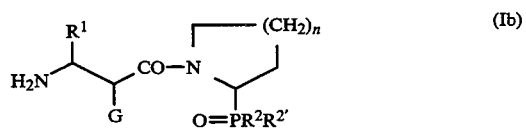

in which $R^1$, $R^2$, $R^{2'}$, G and n have the abovementioned meaning,
are condensed via the corresponding salts, preferably via the hydrochlorides,
either with compounds of the general formula (II)

in which
W has the abovementioned meaning and
A', B' and D' in each case have the abovementioned meaning of A, B and D but do not simultaneously represent a bond,
with activation of the carboxylic acid, if appropriate in the presence of a base and of an auxiliary, in one step or successively (depending on the meaning of the substituents A', B' and D'),
or with compounds of the general formula (III) or (IV)

in which
W has the abovementioned meaning,
X represents halogen, preferably chlorine, and
W' represents the group $CF_3CO-$ or $CH_3CO-$, by the conditions customary in peptide chemistry, in inert solvents, in the presence of a base, or
[B] in the case in which L represents the —$CH_2$ group, compounds of the general formula (V) or (VI)

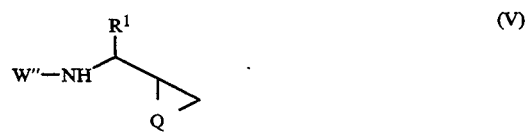

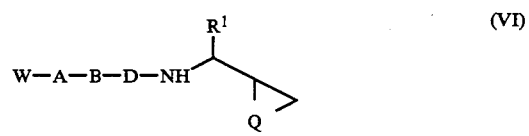

in which
$R^1$, W, A, B and D have the abovementioned meaning,
Q represents oxygen or sulphur and
W'' represents an amino protecting group, preferably BOC,
are reacted with compounds of the general formula (VII)

in which $R^2$, $R^{2'}$ and n have the abovementioned meaning, in inert solvents, if appropriate under pressure, and in the case of the compounds of the general formula (V) the protecting group W'' is then removed by a customary method and, if appropriate, reacted further with the compounds of the general formula (II) by the method described under process [A], or
[C] in the case in which L represents the CO group, compounds of the general formula (VIII)

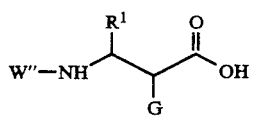
(VIII)

in which W''', G and $R^1$ have the abovementioned meaning, are reacted with the compounds of the general formula (VII) with activation of the carboxylic acid, in the presence of a base and of an auxiliary and the group W—A'—B'—D'—OH is introduced by the method indicated under [A], if appropriate with removal of the protecting group W'''.

The process according to the invention can be illustrated by way of example by the following equation:

[A]

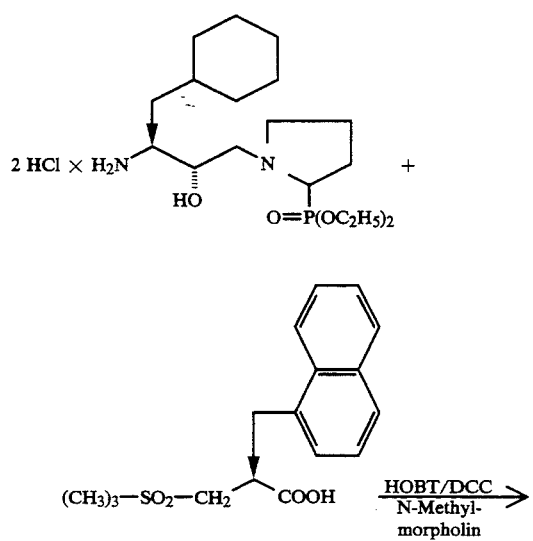

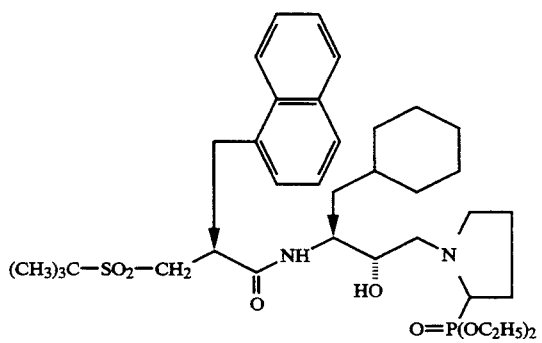

[B]

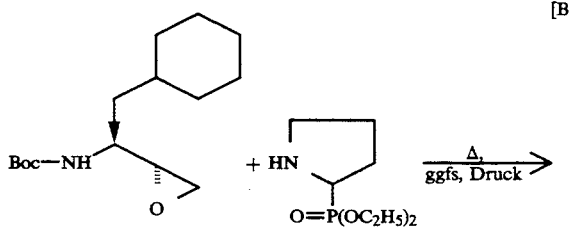

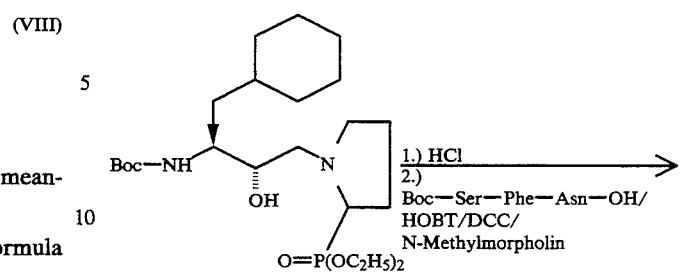

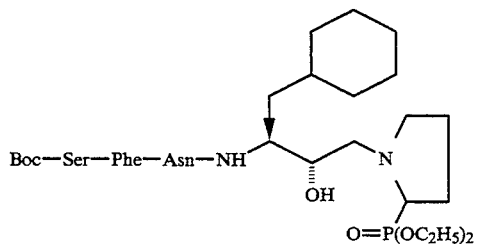

[C]

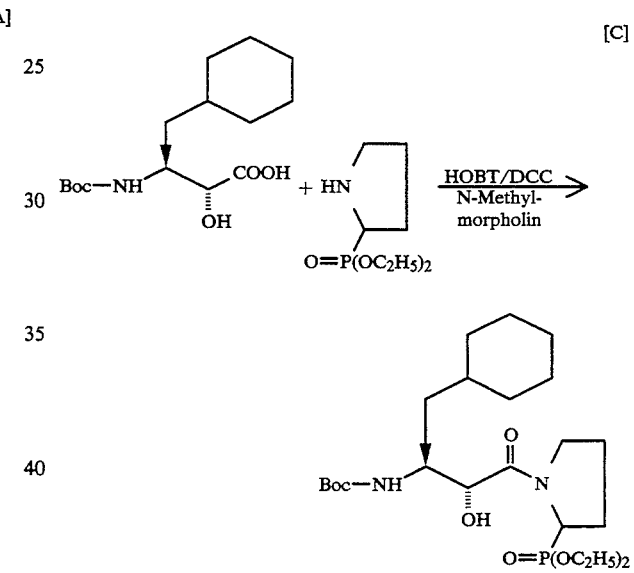

Suitable solvents for all process steps are the customary inert solvents which do not change under the reaction conditions. These preferably include organic solvents such as ethers, for example diethyl ether, glycol monomethyl ether or glycol dimethyl ether, dioxane or tetrahydrofuran, or hydrocarbons such as benzene, toluene, xylene, cyclohexane or mineral oil fractions or halogenohydrocarbons such as methylene chloride, chloroform, carbon tetrachloride, or dimethyl sulphoxide, dimethylformamide, hexamethylphosphoric triamide, ethyl acetate, pyridine, triethylamine or picolines. It is also possible to use mixtures of the solvents mentioned. Dichloromethane, chloroform, dimethylformamide or tetrahydrofuran are particularly preferred.

The compounds of the general formula (II) are known per se and can be prepared by reaction of an appropriate fragment, composed of one or more amino acid groups, having a free carboxyl group which, if appropriate, is present in activated form, with a complementary fragment, composed of one or more amino acid groups, having an amino group, if appropriate in activated form, and by repeating this process with appropriate fragments, protecting groups can then be removed if appropriate or replaced by other protecting groups [cf. Houben-Weyl, Methoden der organischen Chemie, Synthese von Peptiden II (Methods of Organic Chemistry, Synthesis of Peptides II), 4th edition, Vol. 15/1, 15/2, Georg Thieme Verlag, Stuttgart].

Auxiliaries employed for the respective peptide couplings and for the introduction of the radical W (III), (IV) and of the phosphonate ring of the formula (VII) are preferably condensing agents which can also be bases, in particular if the carboxyl group is activated as the anhydride. The customary condensing agents are preferred here, such as carbodiimides, for example N,N'-diethyl-, N,N'-dipropyl-, N,N'-diisopropyl- and N,N'-dicyclohexylcarbodiimide, N-(3-dimethylaminoisopropyl)—N'-ethylcarbodiimide hydrochloride, N-cyclohexyl—N'-(2-morpholinoethyl)-carbodiimide metho-p-toluenesulphonate, or carbonyl compounds such as carbonyldiimidazole, or 1,2-oxazolium compounds such as 2-ethyl-5-phenyl-1,2-oxazolium-3-sulphate or 2-tert-butyl-5-methylisoxazolium perchlorate, or acylamino compounds such as 2-ethoxy-1-ethoxycarbonyl-1,2-dihydroquinoline, or propanephosphonic anhydride, or isobutyl chloroformate, or benzotriazolyloxy-tris(dimethylamino)phosphonium hexafluorophosphate or 1-hydroxybenzotriazole.

In addition, for example, alkali metal carbonates, for example sodium carbonate or potassium carbonate or sodium hydrogencarbonate or potassium hydrogencarbonate, or organic bases such as trialkylamines, for example triethylamine, N-ethylmorpholine, N-methylpiperidine or N-methylmorpholine can be employed. N-Methylmorpholine is preferred.

The auxiliaries and bases are employed in an amount of 1.0 mol to 3.0 mol, preferably 1.0 to 1.2 mol, in each case relative to 1 mol of the compounds of the general formulae (II), (III), (IV), (VII) and (VIII).

The reactions are carried out in a temperature range from 0° C. to 100° C., preferably at 0° C. to 30° C. and at normal pressure.

The reactions can be carried out both at normal pressure and at elevated or reduced pressure (for example 0.5 to 5 bar), preferably at normal pressure in case [A] and [C] amd at elevated pressure in case [B].

The compounds of the general formula (Ia) are new and can be prepared by process [B] mentioned above.

The compounds of the general formula (Ib) are new and can be prepared by process [C] mentioned above.

The compounds of the general formulae (III) and (IV) are known or can be prepared by a customary method.

The compounds of the general formulae (V) and (VI) are known in some cases [cf. J.O.C. 52, 1487 (1987); J. Med. Chem. 31, 1839 (1988)].

The compounds of the general formula (VI) in which W, $R^1$, Q, A, B and D have the abovementioned meaning, but D does not represent a direct bond, and whose physiologically acceptable salts are new, are likewise pharmacological active compounds and are included in the following under the general formula (VIa).

Compounds of the general formula (VIa) according to the invention also have several asymmetric carbon atoms. They can be present independently of one another in the D- or L-form. The invention includes the optical antipodes as well as the isomer mixtures or racemates. The groups A, B and D are present independently of one another in the optically pure form, preferably in the L-form.

The radical of the general formula (XIII)

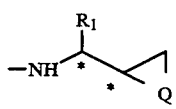

(XIII)

has 2 asymmetric carbon atoms (*), which can be present independently of one another in the R- or S-configuration.

The compounds of the general formula (VIa)

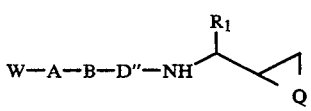

(VIa)

in which
W, A, B, $R^1$ and Q have the abovementioned meaning and
has the abovementioned meaning of D, but does not represent a direct bond, can be prepared by a process in which

[D] in the case in which Q represents an oxygen atom, compounds of the formula (IX)

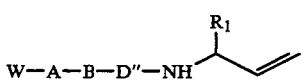

(IX)

in which W, A, B, D" and $R^1$ have the abovementioned meaning,
are reacted in inert solvents using an epoxidation reaction, if appropriate with the aid of a base or of a phase transfer catalysis to give compounds of the general formula (VIb)

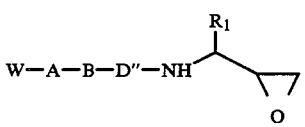

(VIb)

in which W, A, B, D" and $R^1$ have the abovementioned meaning, and

[E] in the case in which Q represents a sulphur atom, the compounds of the general formula (VIb) are further reacted with thiodimethylformamide of the formula (X)

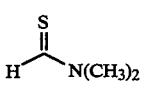

(X)

in inert solvents, in the presence of acids, in a rearrangement reaction to give compounds of the general formula (VIc)

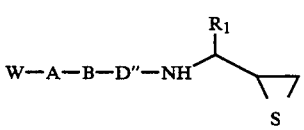

(VIc)

in which W, A, B, D" and $R^1$ have the abovementioned meaning.

The process according to the invention can be illustrated by way of example by the following equation:

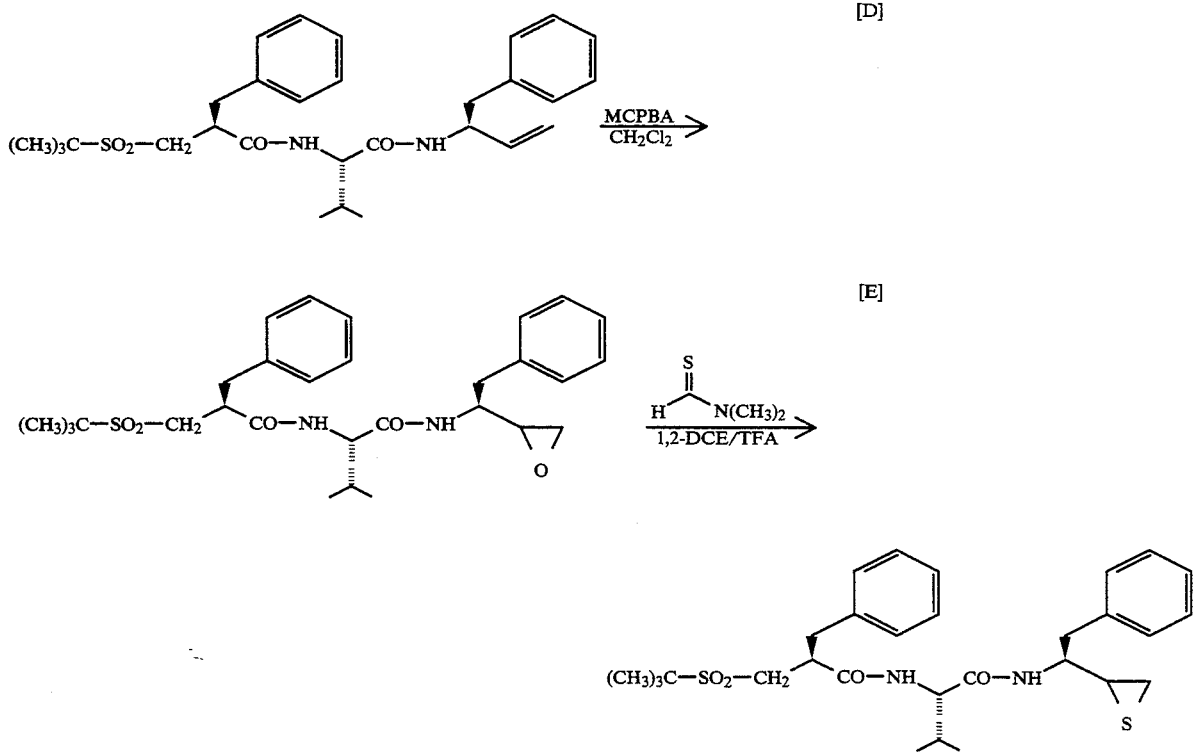

Suitable solvents for processes [D] and [E] are the customary inert solvents which do not change under the reaction conditions. These preferably include organic solvents such as ethers, for example diethyl ether, glycol monomethyl ether or glycol dimethyl ether, dioxane or tetrahydrofuran, or hydrocarbons such as benzene, toluene, xylene, cyclohexane or mineral oil fractions or halogenohydrocarbons such as methylene chloride, dichloroethane (DCE), chloroform, carbon tetrachloride, or dimethyl sulphoxide, dimethylformamide, hexamethylphosphoric triamide, ethyl acetate, pyridine, triethylamine or picoline. It is also possible to use mixtures of the solvents mentioned. Dichloromethane, dichloroethane or chloroform are particularly preferred.

Suitable reagents for the epoxidation are the compounds known from the literature such as, for example, m-chlorobenzoic acid, magnesium monoperoxyphthalate, dimethyldioxirane or methyl(trifluoromethyl)dioxirane. m-Chloroperbenzoic acid and magnesium monoperoxyphthalate are preferred [cf. P. Brongham et al., Synthesis (1987), 1015; W. Adam et al., J. Org. Chem. 52, 2800 (1987) and R. Curci et al., J. Org. Chem. 53, 3890 (1988)].

If the epoxidation is carried out with the aid of a phase transfer catalysis, auxiliaries employed are, for example, organic ammonium chlorides or bromides such as, for example, benzyltriethylammonium chloride or bromide, methyltrioctylammonium chloride, tetrabutylammonium bromide and tricaprylmethylammonium chloride (Aliquat 336). Benzyltriethylammonium chloride and bromide are preferred.

The rearrangement is carried out in analogy to a method known from the literature [cf. T. Takido et al., Synthesis (1986), 779].

Suitable acids for the rearrangement are, for example, methanesulphonic acid, trifluoroacetic acid, trifluoromethanesulphonic acid or tetrafluoroboric acid. Trifluoroacetic acid is preferred.

The acid is employed in an amount from 0.01 mol to 0.1 mol, preferably in catalytic amounts, relative to 1 mol of the compound of the formula (X).

The epoxidation and the rearrangement are carried out in a temperature range from −10° C. to +90° C., preferably from 0° C. to +60° C.

The reactions can be carried out both at normal pressure and at elevated or reduced pressure (for example 0.5 to 5 bar), preferably at normal pressure.

The compounds of the general formula (IX) are new and can be prepared by a process in which

[F] compounds of the general formula (XI)

in which $R^1$ has the abovementioned meaning,
are reacted with compounds of the general formula (IIa)

W—A—B—D''—OH    (IIa)

in which W, A, B and D'' have the abovementioned meaning,
with activation of the carboxylic acid, if appropriate in the presence of a base and of an auxiliary, in one step or successively (depending on the meaning of the substituents A, B and D''), or

[G] compounds of the general formula (IXa)

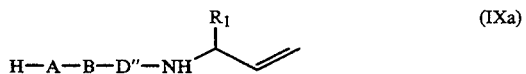

in which A, B, D" and $R^1$ have the abovementioned meaning,
are condensed in inert solvents, in the presence of a base, with the abovementioned compounds of the general formula (III) or (IV)

$$W—X \qquad (III)$$

$$(W')_2O \qquad (IV)$$

in which W, X and W' have the abovementioned meaning,
by the conditions customary in peptide chemistry.

With regard to the choice of the solvents, bases and auxiliaries for processes [G] and [F], the criteria mentioned above under process [A] apply.

The reactions [F] and [G] are carried out in a temperature range from 0° C. to 100° C., preferably at 0° C. to 30° C. and at normal pressure.

The reactions [F] and [G] can be carried out both at normal pressure and at elevated or reduced pressure (for example 0.5 to 5 bar), preferably at normal pressure.

The compounds of the general formula (IXa) are new and can be prepared by the abovementioned process [G].

The compounds of the general formula (XI) are known per se or can be prepared by a method known from the literature [cf. J. R. Luly et al., J. Org. Chem. 52, (1987), 1487].

The compounds of the general formula (VII) are also known [n=1 cf. U.S. Pat. No. 4,186,268; Y. Nomura et al., Chem. Lett., 693 (1977); n=2 cf. V. A. Solodenko et al., Zh. Obshch. Khim. 57, 2392 (1987)].

The compounds of the general formula (VIII) are known or can be prepared by customary methods [cf. DOS 3,825,242; EP 252,727; EP 244,084; U.S. Pat. No. 4,599,198 and EP 266,950].

It has surprisingly been found that the compounds of the general formulae (I) and (VIa) have an extremely strong action against retroviruses. This is confirmed using an HIV-specific protease enzyme test.

The results for the examples listed below were determined by the HIV test system described in the following literature reports [cf. Hansen, J., Billich, S., Schulze, T. Sukrow, S. and Mölling, K. (1988), EMBO Journal, Vol. 7, No. 6, pages 1785–1791]: purified HIV protease was incubated with synthetic peptide which imitates a cleavage site in the Gag precursor protein and represents an in vivo cleavage site of the HIV protease. The resulting cleavage products of the synthetic peptide were analysed by means of reverse phase high performance liquid chromatography (RP-HPLC). The $IC_{50}$ values given relate to the substance concentration which causes a 50% inhibition of protease activity under the abovementioned test conditions.

| Compounds of the general formula (I) | | | |
|---|---|---|---|
| Example No. | $IC_{50}$ (RP-HPLC) (M) | Example No. | $IC_{50}$ (RP-HPLC) (M) |
| 5 (non-polar) | $10^{-6}$ | 26 (polar) | $10^{-7}$ |
| 5 (polar) | $10^{-7}$ | 27 (polar) | $<10^{-8}$ |
| 10 | $5 \times 10^{-8}$ | 28 (non-polar) | $10^{-6}$ |
| 11 | $5 \times 10^{-7}$ | 29 (polar) | $10^{-9}$ |
| 17 | $10^{-8}$ | 30 (polar) | $10^{-7}$ |
| 18 | $10^{-9}$ | 38 (polar) | $5 \times 10^{-7}$ |
| 22 | $10^{-7}$ | 40 (polar) | $5 \times 10^{-7}$ |
| 25 | $10^{-6}$ | | |

| Compounds of the general formula (VIa) | | |
|---|---|---|
| Example No. | $IC_{50}$(RP-HPLC) (M) HIV-1 | HIV-2 |
| 46 | $5 \times 10^{-9}$ | $10^{-8}$ |
| 48 | $10^{-10}$ | not tested |
| 49 | $10^{-9}$ | not tested |
| 50 | $10^{-9}$ | not tested |
| 52 | $10^{-8}$ | $10^{-9}$ |
| 54 | $10^{-8}$ | $10^{-8}$ |
| 55 | $10^{-8}$ | $5 \times 10^{-8}$ |
| 56 | $10^{-8}$ | not tested |
| 57 | $10^{-7}$ | not tested |
| 59 | $10^{-8}$ | $10^{-9}$ |
| 60 | $10^{-9}$ | $5 \times 10^{-8}$ |
| 61 | $5 \times 10^{-8}$ | not tested |
| 62 | $10^{-8}$ | $5 \times 10^{-7}$ |
| 63 | $10^{-8}$ | $10^{-6}$ |
| 64 | $5 \times 10^{-7}$ | not tested |
| 65 | $10^{-6}$ | " |
| 66 | $10^{-7}$ | " |
| 78 | $10^{-7}$ | " |

The compounds according to the invention additionally showed action in cell cultures infected with lentivirus. It was possible to show this by the example of the HIV virus.

HIV Infection in Cell Culture

The HIV test was carried out with slight modifications by the method of Pauwels et al. (Journal of Virological Methods 20 (1988) 309–321).

Normal human blood lymphocytes (PBLs) were concentrated by means of Ficoll-Hypaque and stimulated with phytohaemagglutinin (90 μg/ml) and interleukin 2 (40 U/ml) in RPMI 1640 and 20% foetal calf serum. For infection with the infectious HIV, PBLs were pelleted and the cell pellet was then suspended in 1 ml of HIV virus adsorption solution and incubated at 37° C. for 1 hour.

The virus adsorption solution was centrifuged and the infected cell pellet was taken up in growth medium such that a concentration of $1 \times 10^5$ cells per ml was established. The cells infected in this way were pipetted into the wells of 96-well microtitre plates at a concentration of $1 \times 10^4$ cells/well.

The first vertical row of the microtitre plate contained only growth medium and cells which had not been infected, but otherwise treated exactly as described above (cell control). The second vertical row of the microtitre plate contained only HIV-infected cells (virus control) in growth medium. The other wells contained the compounds according to the invention at different concentrations, starting from the wells of the 3rd vertical row of the microtitre plate, from which the test compounds were diluted 10 times in two-fold steps.

The test batches were incubated at 37° C. until, in the untreated virus control, the syncytia formation typical for HIV occurred (between day 3 and 6 after infection), which was then evaluated microscopically. In the untreated virus control, about 20 syncytia resulted under these test conditions, while the untreated cell control exhibited no syncytia.

The $IC_{50}$ values were determined as the concentration of the treated and infected cells at which 50% (about 10 syncytia) of the virus-induced syncytia were suppressed by treatment with the compound according to the invention.

| Example No.: | IC$_{50}$ (μM) |
|---|---|
| general formula (I) 27 | 9.5 |
| general formula (I) 29 | 4.7 |
| general formula (I) 32 | 5.7 |
| general formula (VIa) 49 | 10 |

It was found that the compounds according to the invention protect HIV-infected cells from virus-induced cell destruction.

The compounds according to the invention are suitable as active compounds in human and veterinarymedicine for the treatment and prophylaxis of diseases caused by retroviruses.

Examples of indication areas which can be mentioned in human medicine are:
1. The treatment or prophylaxis of human retrovirus infections.
2. For the treatment or prophylaxis of diseases (AIDS) caused by HIV I (human immunodeficiency virus; earlier called HTLV III/LAV) and by HIV II and the stages associated therewith such as ARC (AIDS-related complex) and LAS (lymphadenopathy syndrome) and also the immunodeficiency and encephalopathy caused by this virus.
3. For the treatment or the prophylaxis of an HTLV I or HTLV II infection.
4. For the treatment or the prophylaxis of the AIDS-carrier state (AIDS-transmitter state).

Examples of indications in veterinary medicine which can be mentioned are:
Infections with
a) Maedi-visna (in sheep and goats)
b) progressive pneumonia virus (PPV) (in sheep and goats)
c) caprine arthritis encephalitis virus (in sheep and goats)
d) Zwoegerziekte virus (in sheep)
e) infectious anaemia virus (of the horse)
f) infections caused by the feline leukaemia virus
g) infections caused by the feline immunodeficiency virus (fly)
h) infections caused by the simian immunodeficiency virus (siv).

The abovementioned items 2, 3 and 4 are preferred from the indication area in human medicine.

The present invention includes pharmaceutical preparations which contain one or more compounds of the formulae (I) and (VIa) or which consist of one or more active compounds of the formula (I) or (VIa) in addition to non-toxic, inert pharmaceutically suitable excipients, and processes for the production of these preparations.

The active compounds of the formulae (I) and (VIa) are intended to be present in the abovementioned pharmaceutical preparations, preferably in a concentration of about 0.1 to 99.5, preferably from about 0.5 to 95% by weight, of the total mixture.

The abovementioned pharmaceutical preparations may also contain other pharmaceutical active compounds in addition to the compounds of the formulae (I) and (VIa).

The abovementioned pharmaceutical preparations are prepared in a customary manner by known methods, for example by mixing the active compound or compounds with the excipient or excipients.

In general, it has proved advantageous both in human and in veterinary medicine to administer the active compound or compounds of the formulae (I) and (VIa) in total amounts from about 0.5 to about 500, preferably 5 to 100 mg/kg of body weight every 24 hours, if desired in the form of several individual doses, in order to achieve the desired results. An individual dose contains the active compound or compounds preferably in amounts from about 1 to about 80, in particular 1 to 30 mg/kg of body weight. However, it may be necessary to deviate from the dosages mentioned, in particular depending on the species and the body weight of the subject to be treated, the nature and severity of the disease, the type of preparation and the administration of the medicament and the period or interval within which administration takes place.

APPENDIX TO THE EXPERIMENTAL SECTION

I. List of the Eluent Mixtures Used for Chromatography

I Dichloromethane: methanol
II Toluene: ethyl acetate
III Acetonitrile: water
IV Dichloromethane: methanol: ammonia 9:1:0.1

II. Amino Acids

In general, the configuration is indicated by placing an L or D before the amino acid abbreviation, in the case of the racemate a D,L, it being possible, for simplification, to suppress the indication of configuration in the case of L-amino acids and explicit indication then only taking place in the case of the D-form or of the D,L-mixture.

| Ala | L-alanine |
|---|---|
| Arg | L-arginine |
| Asn | L-asparagine |
| Asp | L-aspartic acid |
| Cys | L-cysteine |
| Gln | L-glutamine |
| Glu | L-glutamic acid |
| Gly | L-glycine |
| His | L-histidine |
| Ile | L-isoleucine |
| Leu | L-leucine |
| Lys | L-lysine |
| Met | L-methionine |
| Pro | L-proline |
| Phe | L-phenylalanine |
| Ser | L-serine |
| Thr | L-threonine |
| Trp | L-tryptophan |
| Tyr | L-tyrosine |
| Val | L-valine |

III. Abbreviations

| Z | benzyloxycarbonyl |
|---|---|
| BOC | tert-butoxycarbonyl |
| CMCT | 1-cyclohexyl-3-(2-morpholinoethyl)-carbodiimide metho-p-toluenesulphonate |
| DCC | dicyclohexylcarbodiimide |
| DMF | dimethylformamide |
| HOBT | 1-hydroxybenzotriazole |
| Mir | myristoyl |
| Ph | phenyl |
| THF | tetrahydrofuran |
| Cha | cyclohexylalanine |
| MCPBA | m-chloroperbenzoic acid |
| MMPP | magnesium monoperoxyphthalate hexahydrate |
| Aib | 2-amino-2-methylpropionic acid |

EXPERIMENTAL SECTION I

Preparation Examples

Example 1

Monosodium 1-{(2S, 3S)-3-[(tert-butoxycarbonyl)amino]-2-hydroxy-4-phenyl-butyl}-(2R,S)-2-(pyrrolidinyl)phosphonate

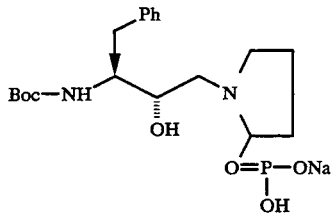

A solution of 1.22 g (8.08 mmol) of 2-phosphonopyrrolidine [U.S. Pat. No. 4,186,268] in 20 ml of water was adjusted to pH 8 by addition of 8 ml of 1 N NaOH solution. A solution of 2.13 g (8.08 mmol) of (1S)-1-[1-(tert-butoxycarbonyl)amino]-2-phenyl-(1S)-ethyl]oxirane [J.R. Luly et al., J. Org. Chem. 52, 1487 (1987)] in 10 ml of acetonitrile was added to this and the stirred mixture was heated at 105° C. in a pressure vessel for 2 h. After cooling, the reaction mixture was poured into 40 ml of water, washed with 50 ml of ethyl acetate, and the aqueous phase was concentrated in vacuo to a volume of about 20 ml and applied to a Lobar ready-to-use column/Merck Lichroprep RP-8 (40–63 μm) size C. The column was eluted with water, which contained an increasing content of acetonitrile. The product-containing fractions were combined and freeze-dried. 1.67 g (47% of theory) of the title compound were obtained as a colourless lyophilisate. $R_f$=0.07, III (4:1)

MS (FAB): m/e=415 (M+H)+, 437 (M+Na)+459 (M+2Na-H)+, 481 (M+3Na-2H)+.

Example 2

1-[(2S, 3S)-3-Amino-2-hydroxy-4-phenyl-butyl]-(2R,S)-2-(pyrrolidinyl)phosphonic acid dihydrochloride

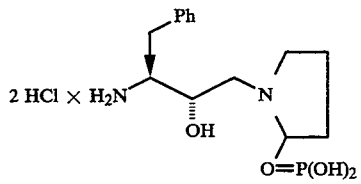

A solution of 1.41 g (2.61 mmol) of the compound from Example 1 in 13 ml of a 4 N solution of gaseous hydrogen chloride in anhydrous dioxane was stirred at 0° C. for 30 min. 10 ml of toluene were then added to this and the mixture was concentrated in vacuo. This process was repeated twice more, then the residue was triturated with ether, filtered off with suction and dried over KOH in a high vacuum. 1.06 g (99% of theory) of the title compound were obtained as a colourless powder.

$R_f$=0.10, III (3:2)

MS (FAB): m/e=315 (M+H)+, 337 (M+Na)+, 359 (M+2Na-H)+

Example 3

Monosodium 1-{(2S, 3S)-3-[[2-(2-aminothiazol-4-yl)-2(Z)-butenoyl]-amino]-2-hydroxy-4-phenyl-butyl}-(2R and 2S)-2-(pyrrolidinyl) phosphonate

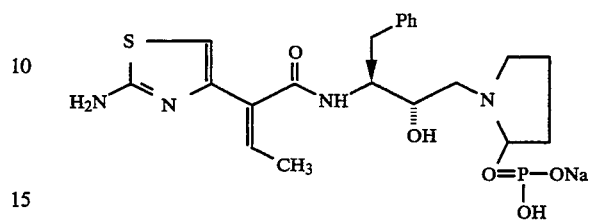

A stirred solution, cooled to 0° C., of 184 mg (1.0 mmol) of 2-(2-aminothiazol-4-yl)-2(Z)-butenoic acid [U.S. Pat. No. 4,500,716] in 4 ml of anhydrous DMF was treated successively with 149 mg (1.10 mol) of HOBT and 206 mg (1.00 mmol) of DCC. The cooling bath was removed and the mixture was stirred at room temperature for 1 h. It was then again cooled to 0° C. and a solution of 375 mg (0.91 mmol) of the compound from Example 2 and 0.32 ml (2.89 mmol) of N-methylmorpholine in 4 ml of DMF was added dropwise. The cooling bath was removed and the mixture was subsequently stirred at room temperature for 16 h. The resulting precipitate was removed by filtration, and the filtrate was treated with 10 ml of toluene and concentrated in vacuo. The foam which remained was taken up in 15 ml of water and adjusted to pH 7.6 by addition of 1N NaOH. The aqueous phase was washed twice with 10 ml of ethyl acetate and then chromatographed on a Lobar ready-to-use column/Merck Lichroprep RP-8 (40–63 μm) size B. The column was eluted with water, which contained an increasing content of acetonitrile. The product-containing fractions were combined and freeze-dried. 58 mg (12% of theory) of the polar diastereomer were obtained.

$R_f$=0.19, III (7:3)

MS (FAB): m/e=481 (M+H)+, 503 (M+Na)+, 525 (M+2Na-H)+

IR (KBr): 3410, 1644, 1632, 1530, 1088, 978 cm$^{-1}$ and 80 mg (16% of theory) of the non-polar diastereomer $R_f$=0.23, III (7:3)

MS (FAB): m/e=481 (M+H)+, 503 (M+Na)+525 (M+2Na-H)+, 547 (M-3Na-2H)+

IR (KBr): 3200–3400, 1656, 1620, 1520, 1088, 978 cm$^{-1}$

Example 4

Diethyl 1-{-(2S, 3S)-3-[(tert-butoxycarbonyl)amino]-2-hydroxy-4-phenylbutyl}-(2R and 2S)-2-(pyrrolidinyl)phosphonate

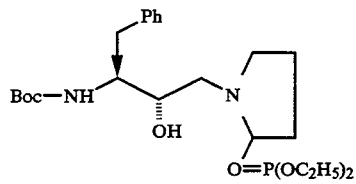

A solution of 2.63 g (10.0 mmol) of (1S)-[1-[1-(tert-butoxycarbonyl)-amino]-2-phenyl-(1S)-ethyl]oxirane [J.R. Lulyetal., J. Org. Chem..52., 487 (1987)] and 2.49 g (12.0 mmol) of diethyl 2-(pyrrolidinyl)phosphonate [U.S. Pat. No. 4,186,268] in 5 ml of n-propanol was stirred at 110° C. in a pressure vessel for 2 h. After cooling, the reaction mixture was concentrated in vacuo and, after prepurification on 100 g of silica gel, separated by chromatography on 400 g of silica gel (toluene:ethyl acetate 1:4).

1.20 g (26% of theory) of the non-polar diastereomer were obtained as an oil.
Rf=0.32, II (1:4)
MS (FAB): m/e=471 (M+H)+, 493 (M+Na)+
and 1.53 g (32% of theory) of the polar diastereomer were obtained as an oil
$R_f$=0.24, II (1:4)
MS (FAB): m/e=471 (M+H)+, 493 (M+Na)+

Example 5

Diethyl 1-{(2S, 3S)-3-[(tert-butoxycarbonyl)-amino]-4-cyclohexyl-2-hydroxy-butyl}-(2R and 2S)-2 (pyrrolidinyl)-phosphonate As described for Example 4, 3.43 g (46% of theory) of the amorphous non-polar diastereomer were obtained as an oil
$R_f$=0.29, II (1:4)
MS (DCI, NH3): m/e=477 (M+H)+
and 2.90 g (39% of theory) of the polar diastereomer were obtained as an oil
$R_f$=0.21, II (1:4)
MS (DCI, NH3): m/e=477 (M+H)+
from 4.25 g (15.78 mmol) of (1S)-1-[1-(tert-butoxycarbonyl)amino]-2-cyclohexyl-(1S)-ethyl]oxirane [J. R. Luly et al., J. Org. Chem. 52, 487 (1987)]and 3.92 g (18.94 mmol) of diethyl 2-(pyrrolidinyl)phosphonate [U.S. Pat. No. 4,186,268] and chromatography of the crude mixture on 830 g of silica gel (toluene:ethyl acetate 1:4).

As described for Example 2, the following products (Table 1) were obtained from the corresponding Boc-protected compounds

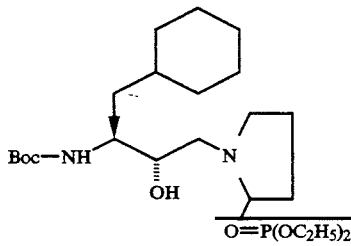

TABLE 1

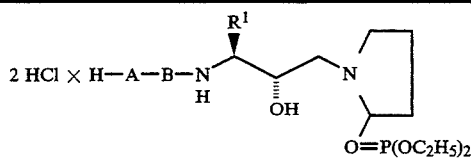

| Example No. | A—B | $R^1$ | Yield (%) | MS (FAB) m/e (M + H)+ | $R_f$/eluent (ratio) | Starting material from Example |
|---|---|---|---|---|---|---|
| 6 | — | PhCH2 | 70 | 371 | 0.48, I (4:1) | 4 (non-polar) |
| 7 | — | PhCH2 | 96 | 371 | 0.43, I (4:1) | 4 (polar) |
| 8 | Val | PhCH2 | 94 | 470 | 0.12, I (9:1) | 16 (non-polar) |
| 9 | Val | PhCH2 | 79 | 470 | 0.11, I (9:1) | 15 (polar) |
| 10 | Phe—Val | PhCH2 | 72 | 617 | 0.29, I (9:1) | 20 |
| 11 | Phe—Val | PhCH2 | 63 | 617 | 0.36, I (9:1) | 19 |
| 12 | — | C6H11-CH2 | 69 | 377 | 0.01, II (1:9) | 5 (non-polar) |
| 13 | — | C6H11-CH2 | 87 | 377 | 0.01, II (1:9) | 5 (polar) |
| 14 | Asn | C6H11-CH2 | 85 | 491[a] | 0.40, I (4:1) | 23 |
| 14a | Val | C6H11-CH2 | 88 | 476 | 0.03, I (9:1) | 31 |
| 14b | Val | C6H11-CH2 | 96 | 476 | 0.02, I (9:1) | 32 |

[a]MS (DCI, NH3): m/e = (M + H)+.

Example 15

Diethyl 1-{(2S, 3S)-3-[(tert-butoxycarbonyl)valinylamino]-2-hydroxy-4-phenyl-butyl}-(2R or 2S)-2-(pyrrolidinyl)-phosphonate MS (FAB): m/e=570 (M+H)+, 592 (M+Na)+

As described for Example 15, the following products (Table 2) were obtained by coupling the corresponding acids with the amine hydrochlorides (starting material):

TABLE 2

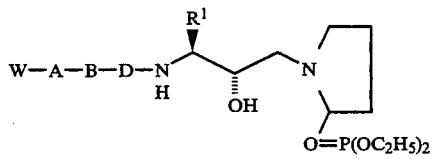

| Example No. | W—A—B—D— | R¹ | Yield (%) | MS (FAB) m/e (M + H)+ | $R_f$/eluent (ratio) | Starting material from Example |
|---|---|---|---|---|---|---|
| 16 | Boc—Val | PhCH₂ | 60 | 570ᵃ | 0.24, I (95:5) | 6 |
| 17 | Boc—Phe—Val | PhCH₂ | 74 | 717 | 0.23, I (95:5) | 8 |
| 18 | Boc—Phe—Val | PhCH₂ | 69 | 717 | 0.18, I (95:5) | 9 |
| 19 | Boc—Phe—Val | PhCH₂ | 48 | 717 | 0.23, I (95:5) | 6 |
| 20 | Boc—Phe—Val | PhCH₂ | 42 | 717 | 0.18, I (95:5) | 7 |
| 21 | Boc—Ser—Phe—Val | PhCH₂ | 15 | 804 | 0.27, I (93:7) | 11 |
| 22 | Boc—Ser—Phe—Val | PhCH₂ | 32 | 804 | 0.19, I (93:7) | 10 |
| 23 | Boc—Asn | cyclohexyl-CH₂ | 17 | 591 | 0.14, I (94:6) | 13 |
| 24 | CH₃(CH₂)₁₂CO—Phe | cyclohexyl-CH₂ | 57 | 735 | 0.15, I (95:5) | 12 |
| 25 | Boc—Ser—Phe—Asn | cyclohexyl-CH₂ | 28 | 825 | 0.31, I (9:1) | 14 |

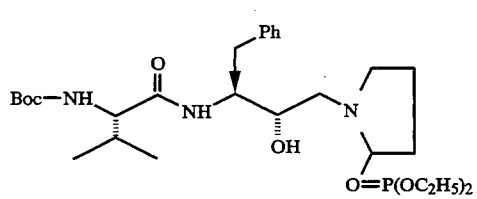

A stirred solution of 429 mg (1.97 mmol) of N-(tert-butoxycarbonyl)-L-valine in 5 ml of anhydrous DMF was treated at 0° C. with 293 mg (2.17 mmol) of HOBT and 876 mg (2.07 mmol) of CMTC. The cooling bath was removed and the mixture was stirred at room temperature for 1 h. The mixture was then cooled to 0° C. again and a solution of 795 mg (1.79 mmol) of the polar diastereomer from Example 7 and 0.69 ml (6.27 mmol) of N-methylmorpholine in 4 ml of DMF was added. The cooling bath was removed and the mixture was stirred at room temperature for 16 h. It was then concentrated in vacuo and the residue was partitioned between 40 ml of ethyl acetate and 40 ml of water. The aqueous phase was extracted with 10 ml of ethyl acetate, and the combined extracts were washed with 50 ml of water and dried over MgSO₄. After evaporation of the solvent in vacuo and chromatography of the crude product on 210 g of silica gel (dichloromethane:methanol 95:5), 581 mg (57% of theory) of the title compound were obtained as an oil.

$R_f$=0.08, I (95:5), polar diastereomer

Example 26

Diethyl 1-{(3S, 4S)-4-[(2S)-3-(tert-butylsulphonyl)-2-(1-naphthylmethyl)propanoyl]valinylamino]-5-cyclohexyl-3-hydroxy-pentanoyl}-(2R or 2S)-2-(pyrrolidinyl)phosphonate

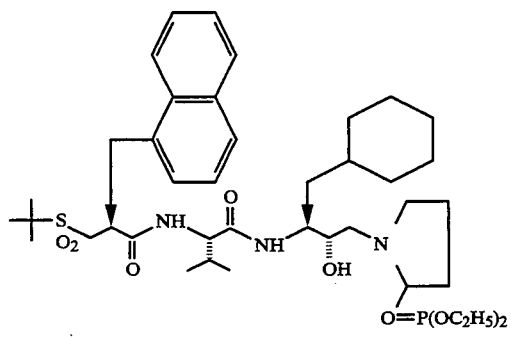

A stirred solution, cooled to 0° C., of 126 mg (0.38 mmol) of (2S)-3-tert-butylsulphonyl-2-(1-naphthylmethyl)propionic acid [prepared according to H. Bühlmayer et al., J. Med. Chem. 31, 1839 (1988)] and 56 mg (0.42 mmol) of HOBT in 4 ml of anhydrous dichloromethane was treated with 82 mg (0.40 mmol) of DCC and the mixture was stirred for 5 min. A solution of 188 mg (0.34 mmol) of the compound from Example 14a and 0.13 ml (1.19 mmol) of N-methylmorpholine in 3 ml of dichloromethane was then added dropwise and the reaction was stirred at room temperature for 1 h. The resulting urea was removed by filtration, the filtrate was concentrated in vacuo and the crude product was purified by chromatography on 33 g of silica gel (dichloromethane:methanol 95:5). 194 mg (72% of theory) of the title compound were obtained as a colourless foam.

$R_f$=0.25, I (95:5) non-polar diastereomer
MS (FAB): m/e=792 (M+H)$^+$.

As described for Example 26, the following products (Table 3) were obtained by coupling the corresponding acids with the amine hydrochloride (starting material):

TABLE 3

W—A—B—D—NH—CHR$^1$—CH(OH)—CH$_2$—N(pyrrolidine with O=P(OC$_2$H$_5$)$_2$ substituent)

| Example No. | W—A—B—D— | R$^1$ | Yield (%) | MS (FAB) m/e (M + H)$^+$ | $R_f$/eluent (ratio) | Starting material from Example |
|---|---|---|---|---|---|---|
| 27 | naphthyl-SO$_2$-CH$_2$CH$_2$-C(O)-Val | cyclohexyl-CH$_2$ | 62 | 792 | 0.24, I (95:5) | 14b (polar) |
| 28 | naphthyl-SO$_2$-CH$_2$CH$_2$-C(O)-Val | PhCH$_2$ | 64 | 786 | 0.17, I (95:5) | 8 (non-polar) |
| 29 | naphthyl-SO$_2$-CH$_2$CH$_2$-C(O)-Val | PhCH$_2$ | 53 | 786 | 0.12, I (95:5) | 9 (polar) |
| 30 | Boc—NH—CH(CH$_2$-cyclohexyl)—C(O)—Val | PhCH$_2$ | 60 | 723 | 0.16, I (95:5) | 9 |
| 31 | Boc—Val | cyclohexyl-CH$_2$ | 69 | 576 | 0.20, I (95:5) | 12 |
| 32 | Boc—Val | cyclohexyl-CH$_2$ | 76 | 576 | 0.08, I (93:7) | 13 |

TABLE 3-continued

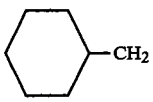

| Example No. | W—A—B—D— | R¹ | Yield (%) | MS (FAB) m/e (M + H)⁺ | $R_f$/eluent (ratio) | Starting material from Example |
|---|---|---|---|---|---|---|
| 33 | Boc—Phe—Val | 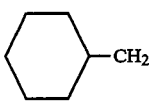 cyclohexyl-CH₂ | 64 | 723 | 0.17, I (94:6) | 14a (non-polar) |
| 34 | Boc—Phe—Val | 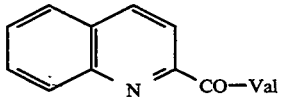 cyclohexyl-CH₂ | 57 | 723 | 0.14, I (94:6) | 14b (polar) |
| 35 | Boc—Phe—Val | PhCH₂ | 63 | 717 | 0.23, I (95:5) | 8 (non-polar) |
| 36 | Boc—Phe—Val | PhCH₂ | 58 | 717 | 0.18, I (95:5) | 9 (polar) |
| 37 | 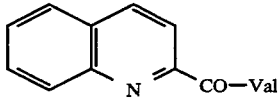 quinoline-2-CO—Val | PhCH₂ | 60 | 625 | 0.25, I (95:5) | 8 |
| 38 | 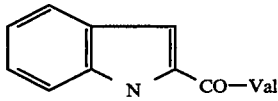 quinoline-2-CO—Val | PhCH₂ | 78 | 625 | 0.24, I (95:5) | 9 |
| 39 | 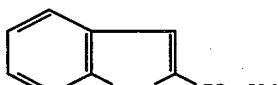 indole-2-CO—Val | PhCH₂ | 75 | 613 | 0.23, I (95:5) | 8 |
| 40 | indole-2-CO—Val | PhCH₂ | 69 | 613 | 0.19, I (95:5) | 9 |

Example 41

Diethyl 1-{(2R, 3S)-3-[(tert-butoxycarbonyl)amino]-2-hydroxy-4-phenylbutyl}-(2R and 2S)-2-(pyrrolidinyl)phosphonate

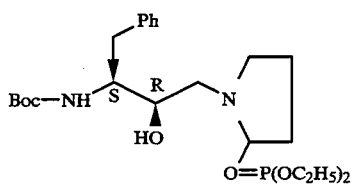

As described for Example 4, 198 mg (12% of theory) of the title compound were obtained as an oil
$R_f$=0.21, II (1:4)
MS (FAB): m/e=471 (M+H)⁺, 493 (M+Na)⁺
from 877 mg (3.33 mmol) of (1R,S)-[1′S-(tert-butoxycarbonyl)amino]-2-phenylethyl]oxirane [J. R. Luly et al., J. Org. Chem. 52, 487 (1987)] and 840 mg (4.0 mmol) of diethyl (2-pyrrolidinyl)phosphonate [U.S. Pat. No. 4,186,268] and complicated chromatographic separation of the crude mixture.

Example 42

Diethyl 1-[(2R, 3S)-3-(amino)-2-hydroxy-4-phenylbutyl]-(2R and 2S)-2-(pyrrolidinyl)phosphonate hydrochloride

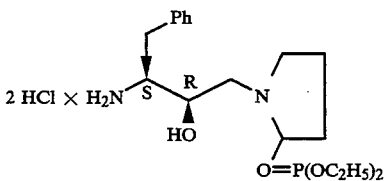

As described for Example 2, 925 mg (93% of theory) of the title compound were obtained as an amorphous powder
$R_f$=0.50, I (8:2)
MS (FAB): m/e=371 (M+H)⁺, 393 (M+Na)⁺
from 1.286 g (2.73 mmol) of the compound from Example 42.

Example 43

Diethyl 1-{(2R, 3S)-3-[(tert-butoxycarbonyl)aspariginylamino]-2-hydroxy-4-phenyl-butyl}-(2R,S)-2-(pyrrolidinyl)phosphonate

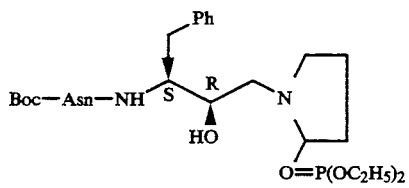

As described for Example 15, 294 mg (33% of theory) of the title compound were obtained as a colourless foam $R_f$=0.30, I (9:1)

MS (FAB): m/e=585 (M+H)+, 607 (M+Na)+ from 892 mg (2.01 mmol) of the compound from Example 42 and 513 mg (2.21 mmol) of N-(tert-butoxycarbonyl)-L-asparagine and chromatography of the crude product on 140 g of silica gel (dichloromethane:methanol, 9:1).

Example 44

Diethyl 1-[(2R, 3S)-3-(asparaginylamino)-2-hydroxy-4-phenylbutyl]-(2R, S)-2 -(pyrrolidinyl)phosphonate hydrochloride

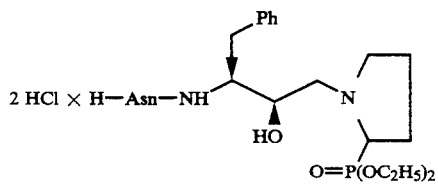

As described for Example 2, 140 mg (69% of theory) of the title compound were obtained as a pale hygroscopic powder decomposition point 191 ° C.

$R_f$=0.35, III (95:5)

MS (FAB): m/e=485 (M+H)+, 507 (M+Na)+ from 210 mg (0.36 mmol) of the compound from Example 43.

Example 45

Diethyl 1-{(2R, 3S)-3-[(2-quinolylcarbonyl)asparaginylamino]-2-hydroxy-4-phenyl-butyl}-(2R, S)-2-(pyrrolidinyl)phosphonate

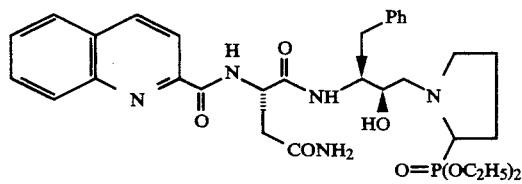

As described for Example 15, 69 mg (43% of theory) of the title compound were obtained as a colourless foam $R_f$=0.14, I (9:1)

MS (FAB): m/e=640 (M+H)+ from 120 mg (0.25 mmol) of the compound from Example 44 and 47 mg (0.26 mmol) of quinoline-2-carboxylic acid and chromatography of the crude product on 12 g of silica gel (dichloromethane:methanol, 9:1).

EXPERIMENTAL SECTION II

Starting compounds

Example I (S)-2-Amino-1-phenylbut-3-ene hydrochloride

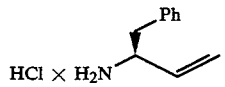

A solution of 5.00 g (20.21 mmol) of (S)-2-(tert-butoxycarbonylamino-1-phenylbut-3-ene [J. R. Luly et al., J. Org. Chem. 52, 1487 (1987)] in 100 ml of a 4N solution of gaseous hydrogen chloride in anhydrous dioxane was stirred at room temperature for 30 min. 15 ml of toluene were then added and the mixture was concentrated in vacuo. This process was repeated twice more, then the residue was triturated with a little ether, filtered off with suction and dried in a high vacuum over KOH. 3.69 g (99% of theory) of the title compound were obtained as colourless crystals.

$R_f$=0.67, eluent mixture IV

MS (DCI, NH3): m/e=148 (M+H)+

Example II (S)-2-Amino-1-cyclohexylbut-3-ene hydrochloride

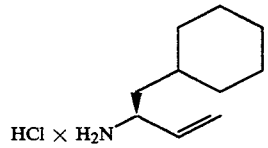

As described for Example I, 3.76 g (99% of theory) of the title compound were obtained as colourless crystals from 5.07 g (20.00 mmol) of (S)-2-(tert-butoxycarbonylamino-1-cyclohexylbut-3-ene [J. R. Luly et al., J. Org. Chem. 52, 1487 (1987)].

Melting point: 232°-233° C.

$R_f$=0.42, III (9:1)

MS (EI, 70 eV) m/e=153 (M)+

Example III (2S)-2-[N-(tert-Butoxycarbonyl-L-valinyl]amino-1-phenylbut-3-ene

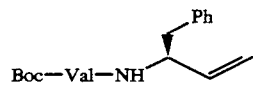

A stirred solution, cooled to 0° C., of 4.81 g (22.13 mmol) of N-(tert-butoxycarbonyl)-L-valine and 3.29 g (24.35 mmol) of HOBT in 40 ml of anhydrous dichloromethane was treated with 5.29 g (25.65 mmol) of DCC and the mixture was stirred for 5 min. A solution of 3.70 g (20.12 mmol) of the compound from Example I and 8.85 ml (80.48 mmol) of N-methylmorpholine in 30 ml of dichloromethane was then added dropwise. The cooling bath was removed and the reaction mixture stirred at room temperature for 2 h. The end of the reaction was determined by thin layer chromatography. The resulting urea was removed by filtration, the filtrate was concentrated in vacuo and the crude product was purified by chromatography on 450 g of silica gel (dichloromethane/methanol 95:5). 6.07 g (87% of theory) of the title compound were obtained as a colourless foam.

$R_f=0.41$, IV
MS (DCI, NH$_3$): m/e=347 (M+H)$^+$.

Example IV (2S)-2-[N-(tert-butoxycarbonyl)-L-valinyl)]amino-1-cyclohexylbut-3-ene

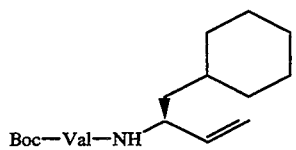

As described for Example III, 4.33 g (65% of theory) of the title compound were obtained as colourless crystals from 3.60 g (19.00 mmol) of the compound from Example II and 4.63 g (21.3 mmol) of Boc-Val-OH.

Melting point: 127°–128° C. (dec.)
$R_f=0.27$, II (9:1)
MS (DCI, NH$_3$) m/e=353 (M+H)$^+$

Example V (2S)-1-Phenyl-2-(N-L-valinyl)aminobut-3-ene hydrochloride

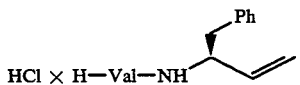

As described for Example I, 4.90 g (99% of theory) of the title compound were obtained as a colourless powder from 6.08 g (17.53 mmol) of the compound from Example III.

$R_f=0.36$, I (9:1)
The following hydrochlorides were obtained as described for Example V:

As described for Example I, 3.37 g (95% of theory) of the title compound were obtained as a colourless powder from 4.32 g (12.30 mmol) of the compound from Example IV.

Melting point: 169°–170° C.
$R_f=0.48$, III (9:1)
MS (DCI, NH$_3$) m/e=253 (M+H)$^+$

Example VII (2S)-2-[N-(2S)-3-(tert-Butylsulphonyl)-2-(1-naphthylmethyl)propanoyl]-L-valinyl]-amino1-phenylbut-3-ene

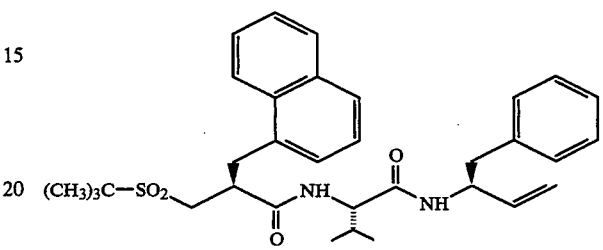

A stirred solution, cooled to 0° C., of 1.50 g (4.47 mmol) of (2S)-3-tert-butylsulphonyl-2-(1-naphthylmethyl)propionic acid [prepared according to H. Bühlmayer et al., J. Med. Chem. 31, 1839 (1988)] and 0.66 g (4.92 mmol) of HOBT in 15 ml of anhydrous dichloromethane was treated with 0.97 g (4.69 mmol) of DCC and the mixture was stirred for 5 min. A solution of 1.15 g (4.07 mmol) of the compound from Example V and 1.80 ml (16.27 mmol) of N-methylmorpholine in 10 ml of dichloromethane was then added dropwise and the reaction was stirred at room temperature for 1 h. The resulting urea was removed by filtration, the filtrate was concentrated in vacuo and the crude product was purified by chromatography on 270 g of silica gel (dichloromethane:methanol 95:5). 2.01 g (88% of theory) of the title compound were obtained as a colourless foam.

$R_f=0.47$, I (95:5)
MS (FAB) m/e=563 (M+H)$^+$

TABLE 4

HCl × H—A—B—D—N⟨R$_1$⟩

| Example No. | H—A—B—D— | R$^1$ | Yield (%) | MS (FAB) m/e (M + H)$^+$ | R$_f$/eluent ratio | Starting material from Example |
|---|---|---|---|---|---|---|
| Va | H—Asn | CH$_2$—C$_6$H$_5$ | 95 | 262 | 0.06, I (9:1) | XXX |
| Vb | H—Aib | CH$_2$—C$_6$H$_5$ | 88 | 233 | 0.50, IV | XXVII |
| Vc | H—Ile | CH$_2$—C$_6$H$_5$ | 98 | 261 | 0,65, IV | XXX |

Example VI (2S)-1-Cyclohexyl-2-(N-L-valinyl)aminobut-3-ene hydrochloride

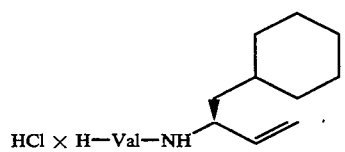

As described for Example VII, the following products (Table 5) were obtained by coupling the corresponding acids with the amine hydrochlorides (starting materials):

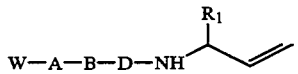

TABLE 5

| Example No. | W—A—B—D— | R¹ | Yield (%) | MS(FAB) m/e (M + H)+ | $R_f$/eluent ratio | Starting material from Example |
|---|---|---|---|---|---|---|
| VIII | (CH₃)₃C—SO₂—CH₂—CH(CH₂-1-naphthyl)—CO—Val | $C_6H_{11}$—$CH_2$ | 76 | 569 | 0.57, I(1:1) | VI |
| IX | (CH₃)₃C—SO₂—CH₂—CH(CH₂-C₆H₅)—CO—Val | $C_6H_5$—$CH_2$ | 92 | 513 | 0.48, I(95:5) | V |
| X | (CH₃)₃C—SO₂—CH₂—CH(CH₂-C₆H₅)—CO—Val | $C_6H_{11}$—$CH_2$ | 75 | 519 | 0.56, II(1:1) | VI |
| XI | CH₃—SO₂—Phe—Val | $CH_2$—$C_6H_5$ | 62 | 472 | 0.12, I(95:5) | V |
| XII | CH₃—SO₂—Phe—Val | $CH_2$—$C_6H_{11}$ | 58 | 478 | 0.50, II(1:1) | VI |
| XIII | CH₃-C₆H₄-SO₂—Phe—Val | $CH_2$—$C_6H_5$ | 29 | 548 | 0.53, I(95:5) | V |
| XIV | CH₃-C₆H₄-SO₂—Phe—Val | $CH_2$—$C_6H_{11}$ | 21 | 554 | 0.70, II(1:1) | VI |
| XV | (CH₃)₃C—CH₂—CO—Phe—Val | $CH_2$—$C_6H_5$ | 80 | 492 | 0.31, I(95:5) | V |
| XVI | (CH₃)₃C—CH₂—CO—Phe—Val | $CH_2$—$C_6H_{11}$ | 57 | 498 | 0.25, I(95:5) | VI |
| XVII | Boc—Phe—Val | $CH_2$—$C_6H_5$ | 74 | 494 | 0.44, I(95:5) | V |
| XVIII | Boc—Phe—Val | $CH_2$—$C_6H_{11}$ | 62 | 500 | 0.38, I(95:5) | VI |
| XIX | Z—Phe—Val | $CH_2$—$C_6H_5$ | 65 | 528 | 0.56, I(95:5) | V |
| XX | Z—Phe—Val | $CH_2$—$C_6H_{11}$ | 75 | 534 | 0.25, I(95:5) | VI |
| XXI | Boc—NH—CH(CH₂-C₆H₁₁)—CO—Val | $CH_2$—$C_6H_5$ | 84 | 500 | 0.43, I(95:5) | V |
| XXII | Boc—NH—CH(CH₂-C₆H₁₁)—CO—Val | $CH_2$—$C_6H_{11}$ | 70 | 506 | 0.38, I(95:5) | VI |
| XXIII | CH₃(CH₂)₁₂—CO—Phe—Val | $CH_2$—$C_6H_5$ | 82 | 604 | 0.34, I(95:5) | V |
| XXIV | quinolin-2-yl—CO—Val | $CH_2$—$C_6H_5$ | 54 | 402 | 0.61, I(95:5) | V |

TABLE 5-continued

| Example No. | W—A—B—D— | R¹ | Yield (%) | MS(FAB) m/e (M + H)+ | $R_f$/eluent ratio | Starting material from Example |
|---|---|---|---|---|---|---|
| XXV | quinoline-2-CO—Val | $CH_2$—$C_6H_{11}$ | 54 | 408 | 0.21, II(4:1) | VI |
| XXVI | indole-2-CO—Val | $CH_2C_6H_5$ | 96 | 390 | 0.51, I(95:5) | V |
| XXVII | Boc—Aib | $CH_2$—$C_6H_5$ | 52 | 333 | 0.51, I(97:3) | V |
| XXVIII | Boc—Phe—Gly—Gly | $CH_2$—$C_6H_5$ | 77 | 509 | 0.45, IV | V |
| XXIX | Boc—Ser—Phe | $CH_2$—$C_6H_5$ | 34 | 482 | 0.45, I(9:1) | V |
| XXX | Boc—Asn | $CH_2$—$C_6H_5$ | 38 | 362 | 0.13, I(95:5) | V |
| XXXI | Boc—Ile | $CH_2$—$C_6H_5$ | 64 | 361 | 0.58, I(97:3) | V |
| XXXII | quinoline-2-CO—Asn | $CH_2$—$C_6H_5$ | 39 | 417 | 0.26, I(95:5) | Va |
| XXXIII | quinoline-2-CO—Aib | $CH_2$—$C_6H_5$ | 70 | 388 | 0.48, II(7:3) | Vb |
| XXXIV | $(CH_3)_3C$—$SO_2$—CH$_2$—CH(naphthyl)—CO—Aib | $CH_2$—$C_6H_5$ | 41 | 549 | 0.35, II(3:2) | Vb |
| XXXV | $(CH_3)_3C$—$SO_2$—CH$_2$—CH(naphthyl)—CO—Ile | $CH_2$—$C_6H_5$ | 72 | 578 | 0.18, II(7:3) | Vc |
| XXXVI | quinoline-2-CO—Ile | $CH_2$—$C_6H_5$ | 94 | 416 | 0.28, II(4:1) | Vc |

PREPARATION EXAMPLES

Example 46

2-{1-[N-[(tert-Butylacetyl)-L-phenylalanyl]-L-valinyl]-amino-2-phenyl-(1S)-ethyl}oxirane

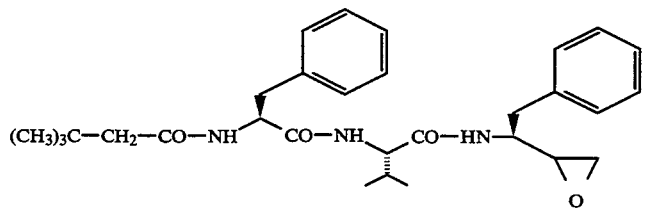

A stirred suspension, cooled to 0° C., of 250 mg (0.60 mmol) of the compound from Example XV in 3 ml of dichloromethane was treated in portions with 259 mg (1.20 mmol—2 equiv.) of m-chloroperbenzoic acid (80% strength) (MCPBA) and the mixture was stirred at this temperature for 2 h. A further 130 mg (0.60 mmol—1 equiv.) of MCPBA were then added and the mixture was subsequently stirred at room temperature for 1 h. 10 ml of ethyl acetate were then added and the reaction mixture was stirred into 20 ml of a 10% strength $Na_2SO_3$ solution. The organic phase was separated off, washed 3 times with 10 ml of $NaHCO_3$ solution and dried over $MgSO_4$. After evaporating the solvent in vacuo and triturating the residue with a little ether/pentane, 253 mg (83% of theory) of the title compound were obtained as a colourless powder.

Melting point: 168° C. (dec.)
$R_f$=0.26, I (97:3)
MS (FAB)m/e=508 (M+H)+

Example 47

(2S)-{1-[N-[(2S)-Benzyl-3-(tert-butylsulphonyl)-propanoyl]-L-valinyl]amino-2-phenyl-(1S)-ethyl}oxirane

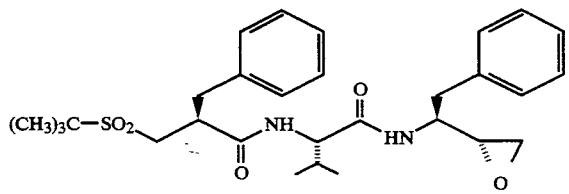

A suspension of 345 mg (0.67 mmol) of the compound from Example IX, 8 mg (5 mol-%) of benzyltriethylammonium chloride and 668 mg (1.35 mmol) of magnesium monoperoxyphthalate hexahydrate (MMPP) in 3 ml of chloroform was adjusted to pH 5 by addition of 1 N NaOH solution and the mixture was heated to reflux for 16 h, a pH of about 5 being maintained by addition of small amounts of 1N NaOH. After cooling, the reaction mixture was filtered with suction and the filtrate was washed with 10 ml of water, 10 ml of 10% strength $Na_2SO_3$ solution and 10 ml of dilute $NaHCO_3$ solution and dried over magnesium sulphate. After evaporation of the solvent in vacuo and chromatography of the residue on 15 g of silica gel (toluene: ethyl acetate 1:1), 131 mg (37% of theory) of the title compound were obtained as a colourless rigid foam.

$R_f$=0.21, II (1:1)
MS (FAB) m/e=529 (M+H)+
HPLC: Mixture of the diastereomeric epoxides (1S): (1R)=16:1

The following epoxides (Table 6) were obtained as described for Example 46:

TABLE 6

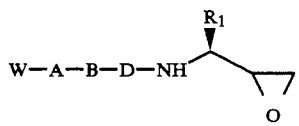

| Example No. | W—A—B—D— | R¹ | Yield (%) | MS(FAB) m/e (M + H)+ | $R_f$/eluent ratio | Starting material from Example |
|---|---|---|---|---|---|---|
| 48 | Z—Phe—Val | $CH_2$—$C_6H_5$ | 81 | 544 | 0.39, I(95:5) | XIX |
| 49 | Boc—Cha—Val | $CH_2$—$C_6H_5$ | 47 | 516 | 0.53, I(95:5) | XXI |
| 50 | (CH₃)₃C—SO₂—CH(CH₂-1-naphthyl)—CO—Val | $CH_2$—$C_6H_5$ | 4 | 579 | 0.16, II(4:6) | VII |
| 51 | (CH₃)₃C—SO₂—CH(CH₂-1-naphthyl)—CO—Val | $CH_2$—$C_6H_5$ | 38 | 579 | 0.12, II(4:6) | VII |
| 52 | (CH₃)₃C—SO₂—CH(CH₂—C₆H₅)—CO—Val | $CH_2$—$C_6H_5$ | 43 | 529 | 0.21, II(1:1) | IX |
| 53 | $CH_3$—$SO_2$—Phe—Val | $CH_2$—$C_6H_5$ | 10 | 488 | 0.22, II(1:1) | XI |
| 54 | $CH_3$—$SO_2$—Phe—Val | $CH_2$—$C_6H_5$ | 39 | 488 | 0.15, II(1:1) | |
| 55 | Boc—Phe—Val | $CH_2$—$C_6H_5$ | 46 | 510 | 0.05, I(97:3) | XVII |

TABLE 6-continued

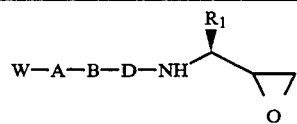

| Example No. | W—A—B—D— | R¹ | Yield (%) | MS(FAB) m/e (M + H)⁺ | R$_f$/eluent ratio | Starting material from Example |
|---|---|---|---|---|---|---|
| 56 | quinoline-2-CO—Val | CH$_2$—C$_6$H$_5$ | 66 | 418 | 0.25, II(7:3) | XXIV |
| 57 | quinoline N-oxide-2-CO—Val | CH$_2$—C$_6$H$_5$ | 22 | 418 | 0.12, II(7:3) | |
| 58 | CH$_3$(CH$_2$)$_{12}$—CO—Phe—Val | CH$_2$—C$_6$H$_5$ | 55 | 620 | 0.33, I(97:3) | XXIII |
| 59 | (CH$_3$)$_3$C—SO$_2$—CH$_2$CH(CH$_2$Ph)—CO—Val | CH$_2$—C$_6$H$_{11}$ | 54 | 535 | 0.12, I(95:5) | X |
| 60 | (CH$_3$)$_3$C—SO$_2$—CH$_2$CH(CH$_2$-naphthyl)—CO—Val | CH$_2$—C$_6$H$_{11}$ | 53 | 585 | 0.28, I(97:3) | VIII |
| 61 | Boc—Phe—Val | CH$_2$—C$_6$H$_{11}$ | 51 | 516 | 0.11, I(97:3) | XVIII |
| 62 | CH$_3$—SO$_2$—Phe—Val | CH$_2$—C$_6$H$_{11}$ | 55 | 494 | 0.13, I(97:3) | XII |
| 63 | (CH$_3$)$_3$C—CH$_2$—CO—Phe—Val | CH$_2$—C$_6$H$_{11}$ | 48 | 514 | 0.12, I(97:3) | XVI |
| 64 | Boc—Cha—Val | CH$_2$—C$_6$H$_{11}$ | 55 | 522 | 0.19, I(97:3) | XXII |
| 65 | Z—Phe—Val | CH$_2$—C$_6$H$_{11}$ | 61 | 550 | 0.34, II(6:4) | XX |
| 66 | Z—Phe—Val | CH$_2$—C$_6$H$_{11}$ | 8 | 550 | 0.14, II(6:4) | XX |
| 67 | Boc—Ser—Phe | CH$_2$—C$_6$H$_5$ | 38 | 500 | 0.12, I(9:1) | XXIX |
| 68 | Boc—Phe—Gly—Gly | CH$_2$—C$_6$H$_5$ | 49 | 525 | 0.41, I(9:1) | XXVIII |
| 69 | quinoline-2-CO—Asn | CH$_2$—C$_6$H$_5$ | 17 | 433 | 0.11, I(95:5) | XXXII |
| 70 | quinoline N-oxide-2-CO—Aib | CH$_2$—C$_6$H$_5$ | 55 | 420 | 0.13, II(3:2) | XXXIII |
| 71 | (CH$_3$)$_3$C—SO$_2$—CH$_2$CH(CH$_2$-naphthyl)—CO—Aib | CH$_2$—C$_6$H$_5$ | 42 | 565 | 0.13, I(93:3) | XXXIV |

TABLE 6-continued

W—A—B—D—NH—C(R₁)H—CH₂—O (epoxide)

| Example No. | W—A—B—D— | R¹ | Yield (%) | MS(FAB) m/e (M + H)⁺ | R_f/eluent ratio | Starting material from Example |
|---|---|---|---|---|---|---|
| 72 | (CH₃)₃C—SO₂—CH₂—CH(CH₂-1-naphthyl)—CO—Ile | CH₂—C₆H₅ | 53 | 594 | 0.18, II(2:3) | XXXV |

Example 73

2-{1-[N-[(2S)-3-(tert-Butylsulphonyl)-2-(1-naphthylmethyl)-propanoyl]-L-valinyl]-amino-2-phenyl-(1S)-ethyl}thiirane

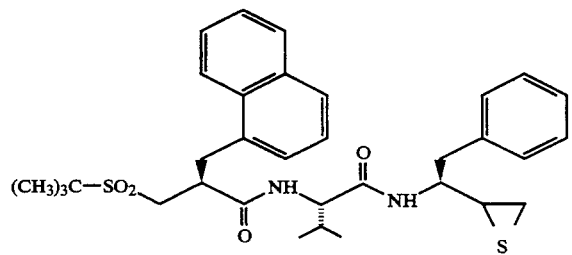

A stirred solution of 159 mg (0.27 mmol) of the compound from Example 51 (polar isomer), 47 μl (0.54 mmol—2 equiv.) of thiodimethylformamide and 2 μl (0.027 mmol—0.1 equiv.) of trifluoroacetic acid in 1 ml of anhydrous dichloroethane (preparation via standard solution) was heated to a bath temperature of 60° C. for 1 h. The reaction mixture was then diluted with 10 ml of ethyl acetate and stirred into a mixture of 10 ml of ethyl acetate, 10 ml of NaHCO₃ solution and 10 ml of NaCl solution. The organic phase was separated off, washed with a mixture of 10 ml of NaHCO₃/NaCl solution (1:1) and dried over MgSO₄. After evaporation of the solvent and chromatography of the crude product on 11 g of silica gel (dichloromethane/methanol 95:5) and then on 6 g of silica gel (toluene:ethyl acetate 4:6), the title compound was obtained as a colourless foam.

$R_f = 0.25$, I (95:5)

MS (FAB) m,/e = 595 (M+H)⁺

As described for Example 73, the following thiiranes (Table 7) were obtained by reaction of the corresponding epoxides:

TABLE 7

W—A—B—D—NH—C(R₁)H—CH₂—S (thiirane)

| Example No. | W—A—B—D— | R¹ | Yield (%) | MS(FAB) m/e (M + H)⁺ | R_f/eluent ratio | Starting material from Example |
|---|---|---|---|---|---|---|
| 74 | (CH₃)₃C—SO₂—CH₂—CH(C₆H₅)—CO—Val | CH₂—C₆H₁₁ | 21 | 551 | 0.14, I(97:3) | 59 |
| 75 | (CH₃)₃C—SO₂—CH₂—CH(CH₂-1-naphthyl)—CO—Val | CH₂—C₆H₁₁ | 31 | 601 | 0.27, II(6:4) | 60 |
| 76 | CH₃—SO₂—Phe—Val | CH₂—C₆H₁₁ | 29 | 510 | 0.17, I(95:5) | 62 |

TABLE 7-continued

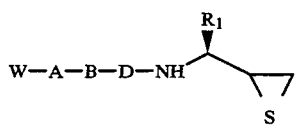

| Example No. | W—A—B—D— | R¹ | Yield (%) | MS(FAB) m/e (M + H)⁺ | R_f/eluent ratio | Starting material from Example |
|---|---|---|---|---|---|---|
| 77 | 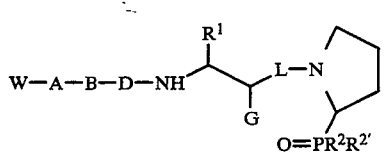 | $CH_2-C_6H_5$ | 24 | 595 | 0.25, I(95:5) | 50 |
| 78 | Boc—Cha—Val | $CH_2-C_6H_5$ | 36 | 538 | 0.35, I(95:5) | 64 |

We claim:

1. A phosphonate-containing pseudopeptide of the formula:

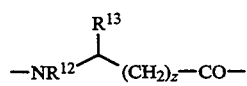

in which:

W
represents hydrogen, tert-butoxycarbonyl or benzyloxycarbonyl; or
represents $R^3$—CO; in which
$R^3$ represents quinolyl, quinolyl-N-oxide, pyridyl, or pyridyl-N-oxide; or represents straight-chain or branched alkyl having up to 13 carbon atoms;
or $R^3$ represents $R^8$—Y—$CH_2$—$CH(R^7)$—; in which
Y represents $SO_2$;
$R^7$ represents phenyl or naphthyl;
$R^8$ represents straight-chain or branched alkyl having up to four carbon atoms;
A, B and D are identical or different and represent a direct bond; or represent a group of the formula:

$$-NR^{12}\overset{R^{13}}{\underset{}{|}}(CH_2)_z-CO-$$

in which
z represents the number 0 or 1;
$R^{12}$ represents hydrogen or methyl; and
$R^{13}$ represents straight-chain or branched alkyl having up to 4 carbon atoms, which is optionally substituted by methylthio, hydroxyl, mercapto, guanidyl, amino, carboxyl, $H_2N$—CO—, cyclohexyl, phenyl, naphthyl, or phenyl or naphthyl substituted by a substituent selected from the group consisting of fluorine, chlorine or alkoxy having up to 4 carbon atoms;
$R^1$ represents straight-chain or branched alkyl having up to 6 carbon atoms, which is optionally substituted by cyclopropyl, cyclopentyl, cyclohexyl or phenyl;

$R^2$ and $R^{2'}$ are identical or different and represent hydroxyl or straight-chain or branched alkoxy having up to 4 carbon atoms;
G represents —SH or —OH; and
L represents —$CH_2$;
or a physiologically acceptable salt thereof.

2. The phosphate-containing pseudopeptide according to claim 1 having the formula:

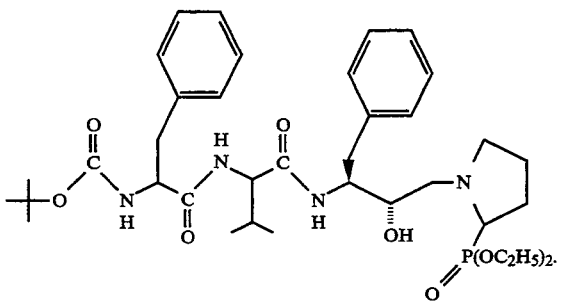

3. The phosphate-containing pseudopeptide according to claim 1 having the formula:

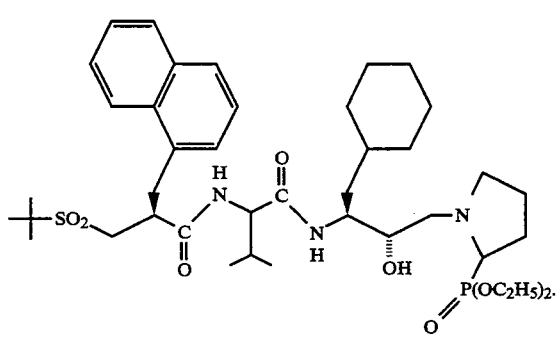

4. The phosphate-containing pseudopeptide according to claim 1 having the formula:

5. The phosphate-containing pseudopeptide according to claim 1 having the formula:
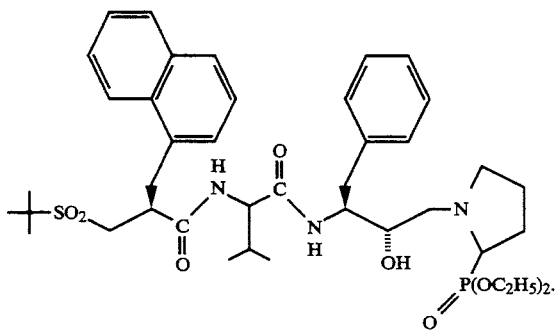
6. The phosphate-containing pseudopeptide according to claim 1 having the formula:
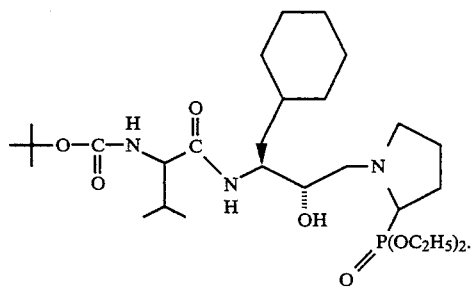
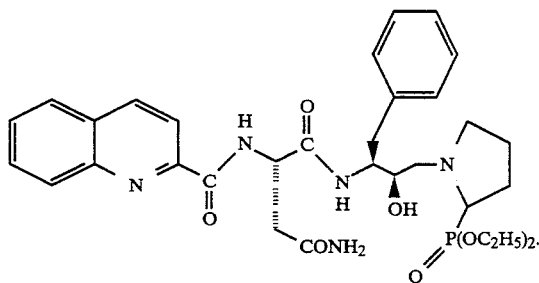
* * * * *